(12) United States Patent
Linares

(10) Patent No.: US 9,271,827 B2
(45) Date of Patent: Mar. 1, 2016

(54) CLAMPING ASSEMBLIES FOR SECURING LIGAMENTS TO A BONE

(71) Applicant: Linares Medical Devices, LLC, Auburn Hills, MI (US)

(72) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 0 days.

(21) Appl. No.: 14/329,031

(22) Filed: Jul. 11, 2014

(65) Prior Publication Data

US 2014/0324168 A1      Oct. 30, 2014

Related U.S. Application Data

(62) Division of application No. 12/797,156, filed on Jun. 9, 2010, now Pat. No. 8,801,784.

(60) Provisional application No. 61/186,215, filed on Jun. 11, 2009.

(51) Int. Cl.
*A61F 2/08* (2006.01)

(52) U.S. Cl.
CPC ......... *A61F 2/0811* (2013.01); *A61F 2002/087* (2013.01); *A61F 2002/0817* (2013.01); *A61F 2002/0823* (2013.01); *A61F 2002/0829* (2013.01); *A61F 2002/0835* (2013.01); *A61F 2002/0847* (2013.01); *A61F 2002/0852* (2013.01); *A61F 2002/0864* (2013.01); *A61F 2002/0882* (2013.01); *A61F 2002/0888* (2013.01); *A61F 2220/0008* (2013.01)

(58) Field of Classification Search
CPC ........................................................ A61F 2/08
See application file for complete search history.

(56) References Cited

U.S. PATENT DOCUMENTS

| | | | | |
|---|---|---|---|---|
| 3,091,828 A | * | 6/1963 | Soltis | A47J 43/18 24/350 |
| 4,548,202 A | * | 10/1985 | Duncan | A61B 17/0643 606/220 |
| 4,744,793 A | | 5/1988 | Parr et al. | |
| 4,772,286 A | | 9/1988 | Goble et al. | |
| 4,870,957 A | | 10/1989 | Goble et al. | |
| 4,997,434 A | | 3/1991 | Seedhom et al. | |
| 5,108,431 A | | 4/1992 | Mansat et al. | |
| 5,147,362 A | | 9/1992 | Goble | |
| 5,207,679 A | | 5/1993 | Li | |
| 5,250,049 A | * | 10/1993 | Michael | A61B 17/683 411/908 |
| 5,314,427 A | | 5/1994 | Goble et al. | |
| 5,458,601 A | | 10/1995 | Young, Jr. et al. | |
| 5,458,636 A | * | 10/1995 | Brancato | A61F 2/0063 606/151 |

(Continued)

*Primary Examiner* — Jacqueline Woznicki
(74) *Attorney, Agent, or Firm* — Dinsmore & Shohl LLP; Douglas J. McEvoy

(57) ABSTRACT

An assembly for securing a plurality of ligaments to a bone includes a first portion exhibited by such as a ring shaped clamp with a tab and slot or a split stem incorporating a plurality of spaced apart ring shaped clamps compressively gripping about the ligaments. A second portion includes at least one of a screw or a ring extending portion engaging a ligament end loop or an undercut recess seating portion extending from an end of a body also incorporating the first portion, and such that the second portion extends from an end of the ligaments and mounts to the bone. The ligaments may further include first and second end-to-end attached sections, between which are configured angled and opposing/aligning incisions.

4 Claims, 12 Drawing Sheets

(56) References Cited

U.S. PATENT DOCUMENTS

| | | | |
|---|---|---|---|
| 5,505,735 A | 4/1996 | Li | |
| 5,575,803 A * | 11/1996 | Cooper | A61B 17/07207 227/175.1 |
| 5,702,397 A | 12/1997 | Goble et al. | |
| 5,800,544 A * | 9/1998 | Demopulos | A61B 17/1146 606/53 |
| 5,916,224 A * | 6/1999 | Esplin | A61B 17/1146 606/151 |
| 5,964,764 A | 10/1999 | West, Jr. et al. | |
| 6,106,556 A * | 8/2000 | Demopulos | A61B 17/1146 606/323 |
| 6,132,442 A | 10/2000 | Ferragamo et al. | |
| 6,221,107 B1 | 4/2001 | Steiner et al. | |
| 6,231,581 B1 * | 5/2001 | Shank | A61B 17/064 606/157 |
| 6,932,841 B2 | 8/2005 | Sklar et al. | |
| 7,156,862 B2 * | 1/2007 | Jacobs | A61B 17/064 606/215 |
| 7,398,907 B2 * | 7/2008 | Racenet | A61B 17/0644 227/176.1 |
| 7,578,844 B2 | 8/2009 | Sklar et al. | |
| 7,665,646 B2 * | 2/2010 | Prommersberger | A61B 17/07207 227/175.1 |
| 8,137,383 B2 | 3/2012 | West, Jr. et al. | |
| 8,801,732 B2 * | 8/2014 | Harris | A61B 17/0644 227/175.1 |
| 2003/0009220 A1 * | 1/2003 | Seyr | A61F 2/0811 623/13.14 |
| 2004/0002735 A1 | 1/2004 | Lizardi et al. | |
| 2004/0010276 A1 * | 1/2004 | Jacobs | A61B 17/064 606/153 |
| 2005/0197699 A1 * | 9/2005 | Jacobs | A61F 2/0811 623/13.14 |
| 2007/0156158 A1 | 7/2007 | Herzberg et al. | |
| 2007/0162022 A1 * | 7/2007 | Zhang | A61B 17/686 606/323 |
| 2008/0288070 A1 | 11/2008 | Lo | |
| 2009/0306777 A1 | 12/2009 | Widmer et al. | |
| 2014/0067061 A1 * | 3/2014 | Kubiak | A61B 17/08 623/13.14 |
| 2015/0245841 A1 * | 9/2015 | Linder | A61B 17/08 606/151 |

* cited by examiner

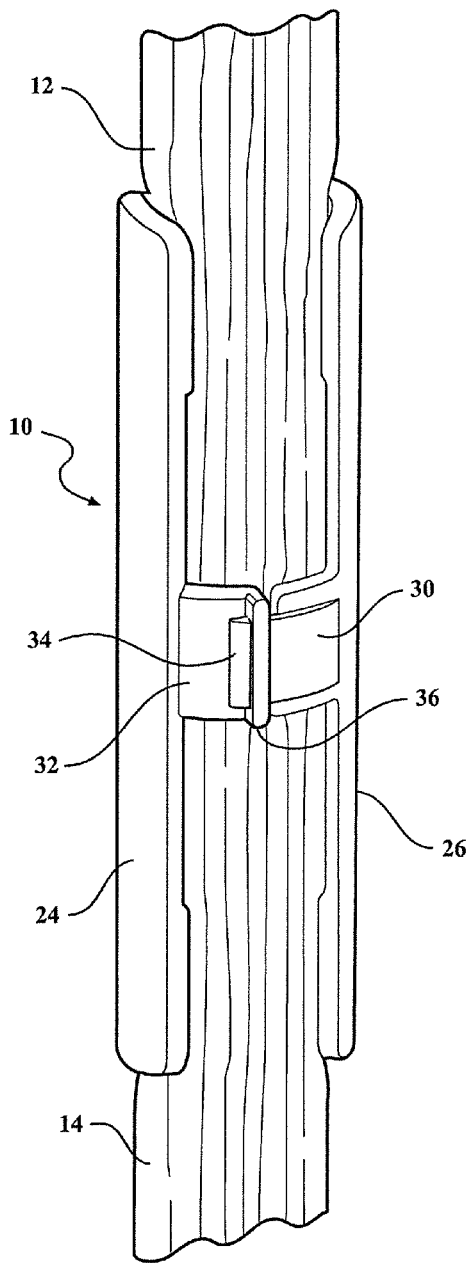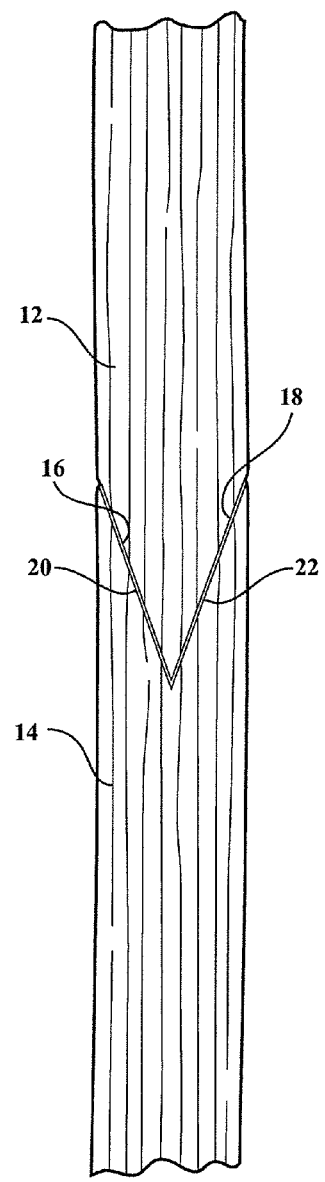
FIG. 1
FIG. 2

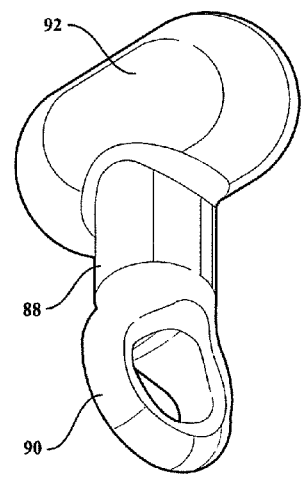
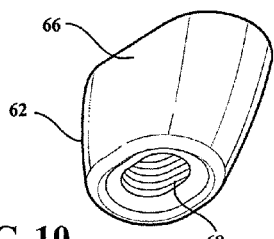
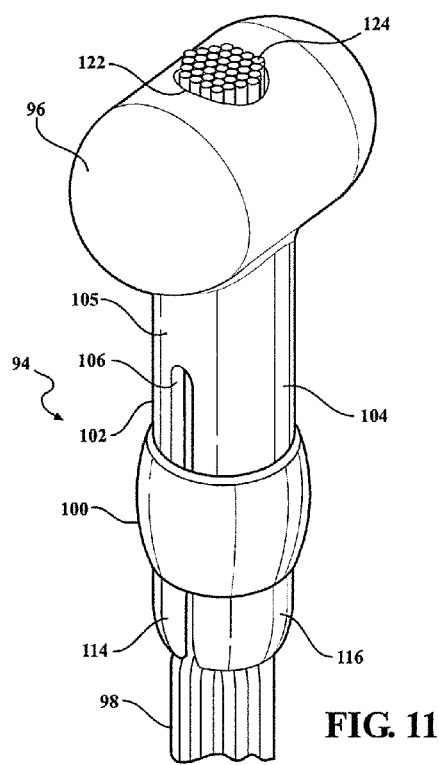
FIG. 10
FIG. 11

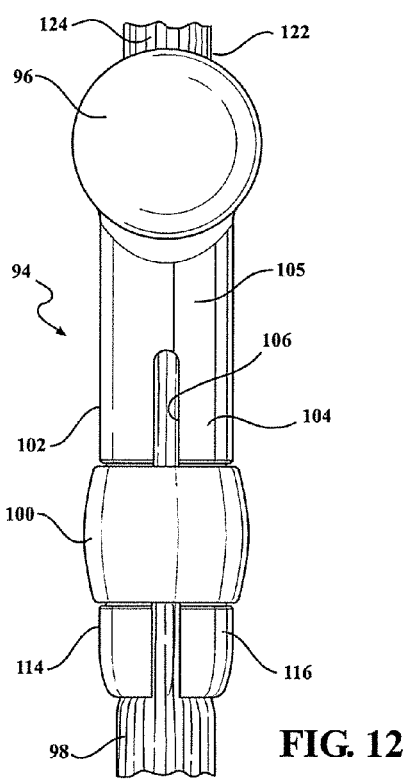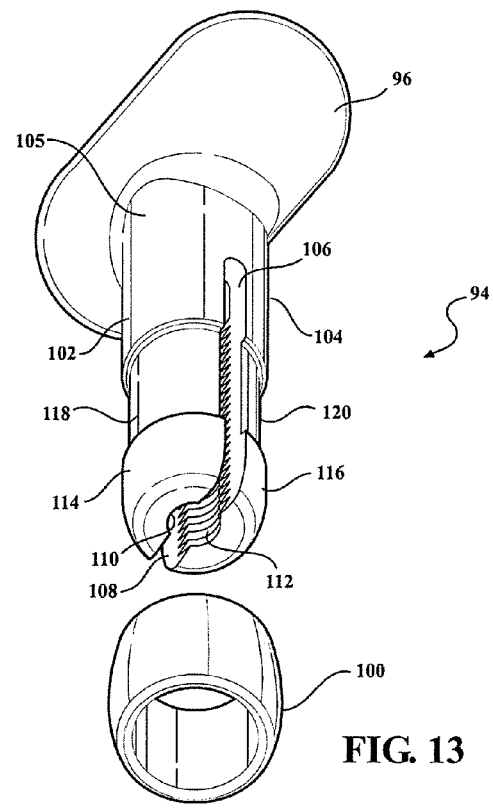
FIG. 12
FIG. 13

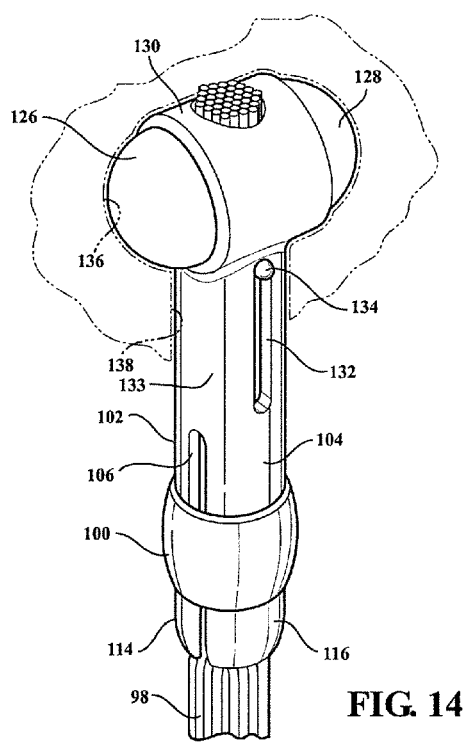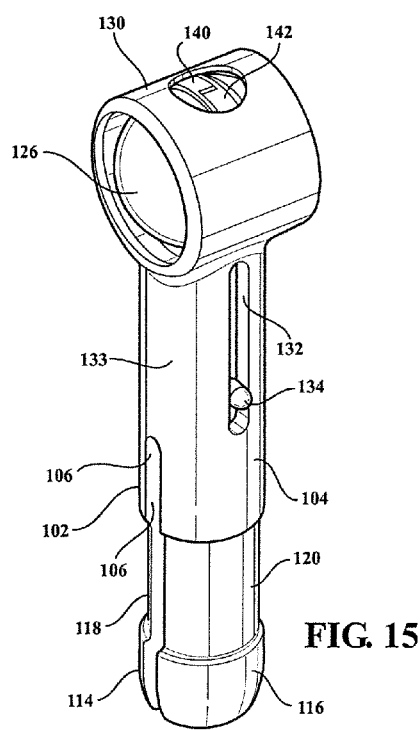

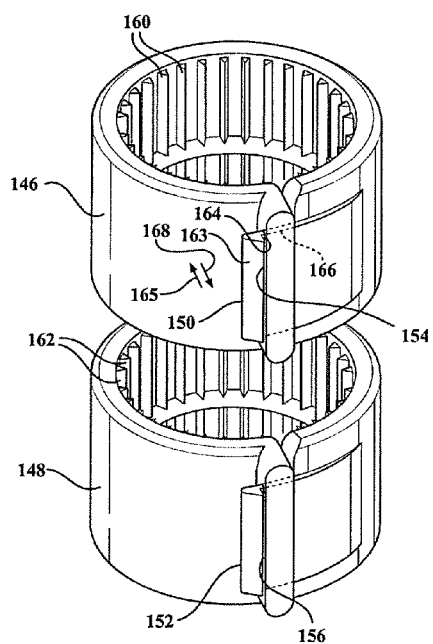 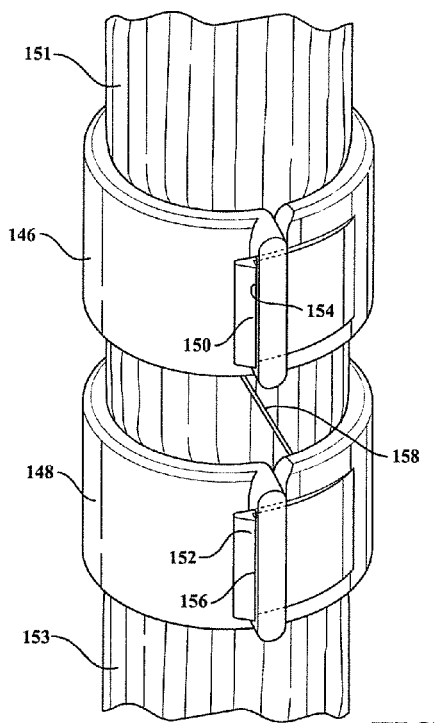
FIG. 18
FIG. 19

CLAMPING ASSEMBLIES FOR SECURING LIGAMENTS TO A BONE

CROSS-REFERENCE TO RELATED APPLICATIONS

This application is a Division of application Ser. No. 12/797,156 filed on Jun. 9, 2010. Application Ser. No. 12/797, 156 claims the benefit of U.S. Provisional Application 61/186,215 filed on Jun. 11, 2009, the contents of which are incorporated herein in their entirety.

FIELD OF THE INVENTION

The present invention teaches various types of clamp or brace assemblies for repairing ligament damage. More specifically, the present invention discloses a variety of braces, clamps and related devices for repairing either natural or synthetic ligaments implanted within a reconditioned or replaced joint assembly.

BACKGROUND OF THE INVENTION

The prior art is documented with various assemblies for repairing or installing artificial ligaments associated with any of a repaired, reconstructed or artificially installed joint implant. A continual objective is the ability to properly size and install ligaments for ensuring long term use of the reconditioned joint.

As is known, a problem with both (natural) existing joint assemblies and artificial implanted joints is the ability to securely anchor and maintain the arrangement of ligaments which are necessary for proper joint operation. It is further known that such ligaments can be damaged apart from the associated joint application, thus requiring repair or replacement. Such artificial ligaments can include such as graphite and composite plasticized constructions, these providing the desired properties of durability combined with stretch resistance.

SUMMARY OF THE INVENTION

The present invention discloses an assembly for securing a plurality of ligaments to a bone and includes a first portion such as a ring shaped clamp with a tab and slot or a split stem incorporating a plurality of spaced apart ring shaped clamps compressively gripping about the ligaments. A second portion includes at least one of a screw or a ring extending portion engaging a ligament end loop or an undercut recess seating portion extending from an end of a body, such as further including first and second split portions incorporating the undercut seating portion, and such that the second portion extends from an end of the ligaments and mounts to the bone.

The ligaments may further include first and second end-to-end attached sections, between which are configured angled and opposing/aligning incisions. Additional features include the first portion ring shaped clamp further exhibiting an inwardly serrated and ligament gripping surface. The undercut recess seating portion further can exhibit first and second trigger displaceable undercut seating portions outwardly displaceable from a housing. The trigger seating portions further can include a slot defined in a stem portion of the body, a button slidable along the slot and actuating a linkage connected to the displaceable seating portions.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is an illustration of a clamping assembly for repairing damaged or broken ligaments according to a first embodiment;

FIG. 2 is an illustration of a plurality of ligaments from FIG. 1 and in which a "V" notch configuration is imparted between refashioned first and second sections of strands, this in order to maximize the holding capabilities provided by the clamping assembly in FIG. 1;

FIG. 10 is an exploded view of the clamp and end anchor of FIG. 9;

FIG. 11 is a perspective illustration of a ligament end mounting clamp according to a still further configuration and including a bone securing end-anchor integrally formed with an elongated stem for supporting about an end of the ligament bunch and which is inwardly compressible by a slidably installed ring clamp;

FIG. 12 is a side view of the installed clap shown in FIG. 11;

FIG. 13 is an exploded perspective of the clamp assembly as depicted in FIGS. 11 and 12 and further illustrating the inwardly serrated surfaces applied along each of the lengthwise extending and linearly separated/compressible halves;

FIG. 14 is a perspective illustration of a ligament end mounting clamp similar in nature to that disclosed in FIG. 11 and further illustrating a pair of semi-spherical undercut seating portions and associated trigger mechanism for outwardly displacing the seating portions from a modified housing associated with the end anchor;

FIG. 15 is an illustration of the ligament end mounting clamp of FIG. 14 and further showing the linear displaceable trigger mechanism associated with a stem portion of the clamp retracted to withdraw the undercut seating portions inwardly within the housing, such as corresponding to an initial bone installation position of the anchor;

FIG. 18 is an illustration of a pair of ring shaped clamps and illustrating inwardly defined serrated teethed patterns for enhancing its gripping properties when installed in compressing fashion over associated ligaments;

FIG. 19 is an environmental view of the pair of ligament compressing clamps depicted in FIG. 18 and further illustrating the incorporation of an angled incision defined in the opposing and mating ends of the ligament sections according to the further preferred configuration;

DETAILED DESCRIPTION OF THE PREFERRED EMBODIMENTS

Referring to the several illustrations, the present invention discloses a variety of clamp and brace assemblies for repairing ligament damage. As previously described, the present invention discloses a variety of braces, clamps and related devices for repairing either natural or synthetic ligaments implanted within a reconditioned or replaced joint assembly.

Additionally, it is understood that ligament repair, reconditioning or replacement can be associated with implantation of an artificial replacement joint. In each below described example, the ability to maintain continuous and non-slipping grip of the ligament strand, combined with the disclosure of effective mechanisms for securely anchoring the ligaments to a bone location, are stressed. The present invention also discloses unique and novel techniques for notching or incising opposing and mating surfaces of first and second individual ligament bunches, these subsequently being securely clamped in place by the various assemblies described herein.

Figure 3:
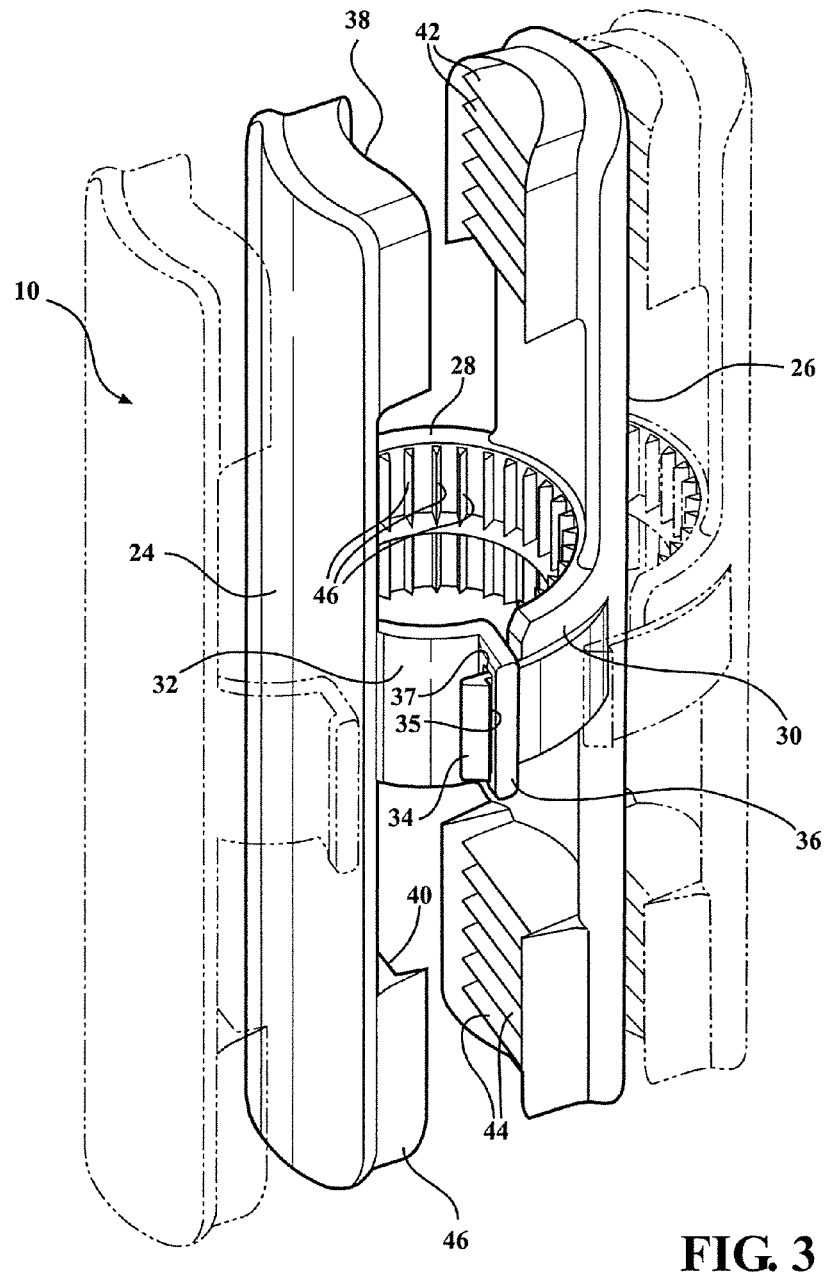
FIG. 3 is a perspective illustration of the clamping assembly of FIG. 1 in both exploded (phantom) and assembled positions.

Referring first to FIGS. 1-3, a series of illustrations are provided of a clamping assembly 10 according to a first non-limiting variant for repairing damaged or broken ligaments, further depicted as first 12 and second 14 end-aligning ligament sections. As best shown in FIG. 2, the end to end aligning and connecting ligament sections (bunches) 12 and 14 are illustrated in which a "V" notch separation line configuration is imparted between refashioned and opposing end connections of the first 12 and second sections 14 strand sections, this creating an overlap configuration between the opposing end portions of the ligament bunches and in order to maximize the holding capabilities provided by the clamping assembly 10 in FIG. 1.

The incised pattern established between the ligament bunches is shown by first end projecting and interconnecting "V" configuring surfaces 16 and 18 associated with the upper ligament bunch 12, a corresponding and mating recess pattern being further defined by additional surfaces 20 and 22 associated with the second lower bunch 14 and within which is seated the projecting profile of upper ligaments 12. Consistent with the description of FIG. 2, it is also understood that the ligament sections as described and illustrated herein envision the use of both individual (and larger diameter sized) ligaments or multiple (plural) ligament bunches, such as described throughout the several views.

As will also be described, the notching or incising of the opposing ends of the ligament sections can be fashioned in varying patterns, the purpose for which being to achieve maximum restraining and location of the sections when gripped between the clamping assembly. It is further envisioned that, in situations where a previously installed ligament is damaged, such notching and subsequent clamping is desirous in a repairing (in situ) operation where the necessary repairs to the patient can be achieved without removal or refashioning of the underlying joint assembly.

As again depicted in FIG. 1 and with further reference to FIG. 3 which illustrates both separated (phantom) and assembled (solid) positions of the clamping assembly 10, the clamping assembly can be constructed of any of a plastic, composite plastic or other hybrid material which exhibits the necessary properties of bend-ability and durability, and which further illustrates the features of first 24 and second 26 lengthwise extending and linearly/circumferentially spaced supports. A generally ring shaped clamping portion 28 is integrally formed with intermediate locations of the lengthwise supports 24 and 26.

The clamping portion 28 exhibits a generally ring shape and, dependent upon the variant, can include first and second split locations defining separable halves or (as further depicted) can define a flexible material which is opened at a single location via a first mounting end 30 and a second circumferentially opposing mounting end 32. The first mounting end 30 exhibits a tab 34 (such as further configuring a ramped or angled portion terminating in an end abutting shoulder 35) and which is engageable within a slot defined within an opposing receiving portion 36 (see further inner perimeter surface 37 which establishes the slot) associated with the second mounting end 32. In this fashion, and as is again shown in FIG. 1, the clamping assembly 10 is capable of being flexibly applied around the interconnecting interface defined between the ligament bunches 12 and 14, following which the tab 34 is engaged through the receiving portion 36.

FIG. 3 further illustrates the clamping assembly 10 in an opened position (see lengthwise supports 24 and 26 in phantom) prior to locating and securing about a repaired ligament configuration (bunches 12 and 14) such as shown in FIG. 2. In combination with the assembled configuration of FIG. 1, FIG. 3 also illustrates the manner in which the elongated supports 24 and 26 are deflected outwardly relative to the interconnecting ring shaped clamping portion 28 and prior to installing about the repair location of the end to end disposed ligament sections 12 and 14. Also included is the provision of inwardly facing and knurled (or teethed) surface patterns for providing an added measure of gripping of the supports 24 and 26 about the ligament bunches, such as which can be incorporated into reinforced portions located at opposing and first and second end locations, see at 38 & 40 and 42 & 44 associated with the supports 24 and 26, as well as additional knurled portions 46 extending inwardly in circumferential fashion around the inner perimeter of the ring clamp portion 28.

In this fashion, the clamping assembly 10 can be manipulated to encircle and subsequently compress and fixedly engage the repaired ligament sections 12 and 14 without fear of the ligaments separating prior to them fusing together. It is also envisioned that the clamp can be sized to become an enduring part of the ligament repair, in particular instances, or can be removed in a subsequent operation once the break in the ligaments has completely healed.

Figure 4:
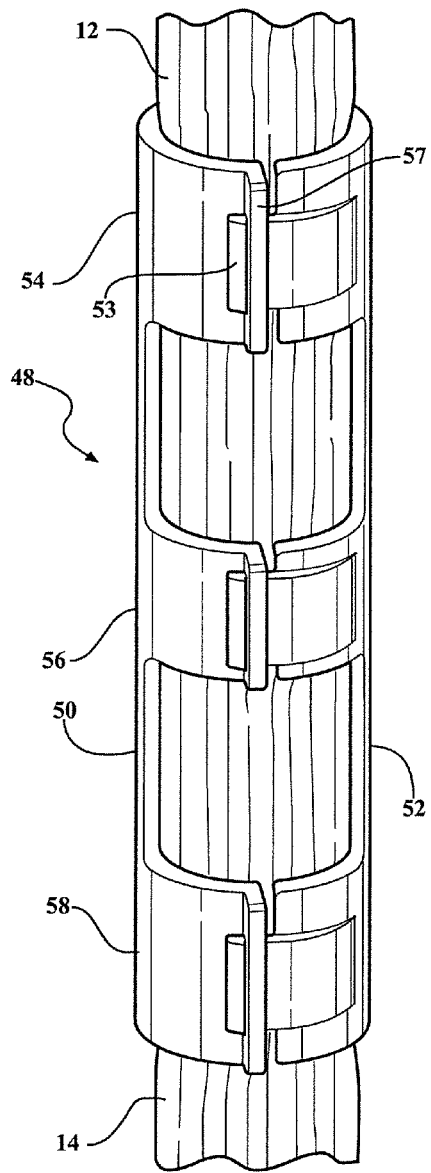
FIG. 4 is an illustration of a modified clamping assembly incorporating a plurality of circumferential extending fastening locations.
Figure 5:
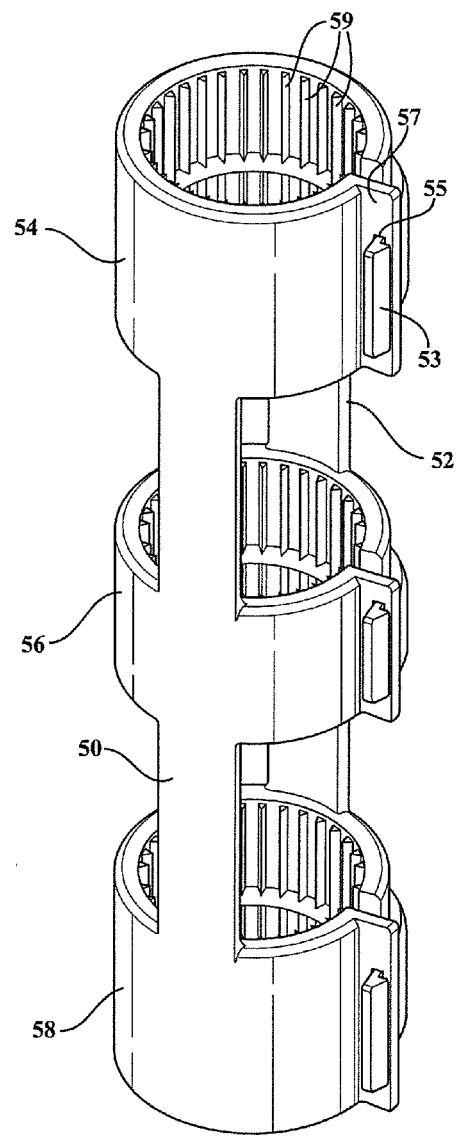
FIG. 5 is a rotated perspective illustration of the clamping assembly in FIG. 4.

Referring now to FIGS. 4 and 5, an illustration is generally shown at 48 a modified clamping assembly incorporating a plurality of circumferential extending and generally ring-shaped fastening locations which generally corresponds to the assembled version of the clamping assembly 10 in FIG. 3. Specifically, a pair of modified and lengthwise supports 50 and 52 are structurally maintained by a plurality of spaced apart, integrally formed and generally ring shaped clamping portions 54, 56 and 58, each of which generally corresponds in construction to the single ring-shaped clamp 28 illustrated in the variant of FIG. 1.

As with the clamp 28, each of the spaced apart clamping portions 54, 56 and 58 is integrally formed with upper/lower end and intermediate locations between the lengthwise supports 50 and 52 and, identical to that described in FIG. 3 with reference to ring clamping portion 28, each further again includes a first mounting end with a first engaging tab (see as is selected shown by tab 53 for upper clamping portion 54) which is received within a slot defined within an opposing receiving portion (further exemplary shown by slot 55 and receiving portion 57) associated with a second mounting end. Also again shown are respective pluralities of inner perimeter surface applied knurled or teethed surface patterns (see as shown by example at 59 for upper clamping portion 54 and which is identical to that previously illustrated at 46 in FIG. 3), which are also identical to that identified and described in the embodiment of FIG. 3 and which facilitate compressive gripping and permanent location about the repaired ligament sections 12 and 14 also depicted in FIG. 4.

Figure 6:
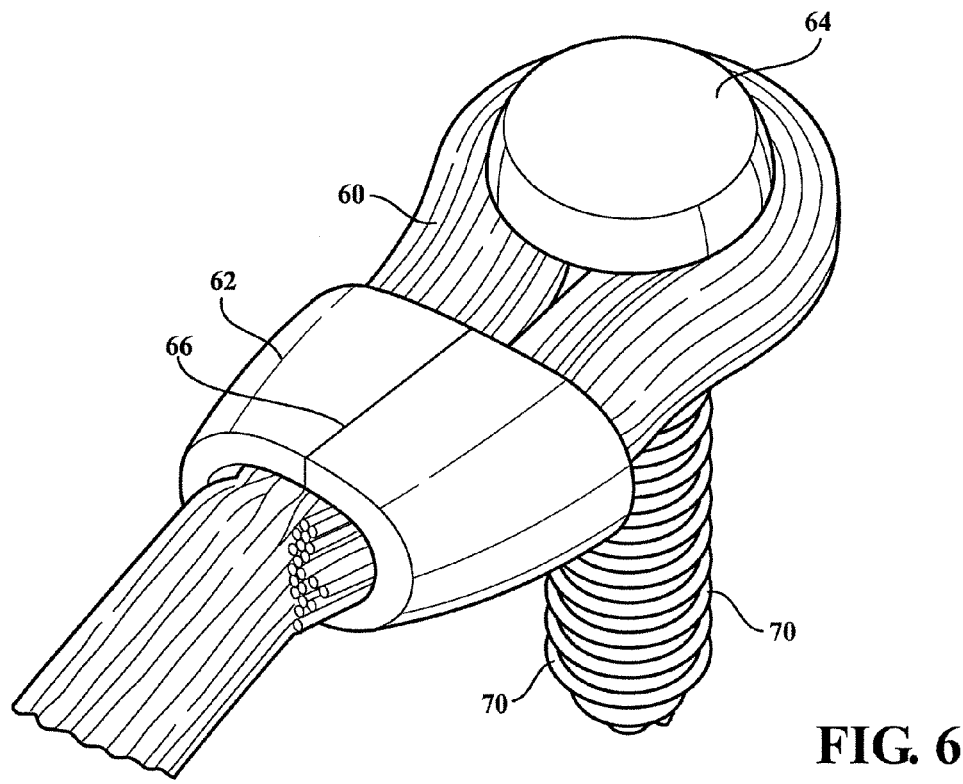
FIG. 6 illustrates an end looped plurality of ligaments mounted to a bone by a combination clamp and bone screw according to a further embodiment.
Figure 7:
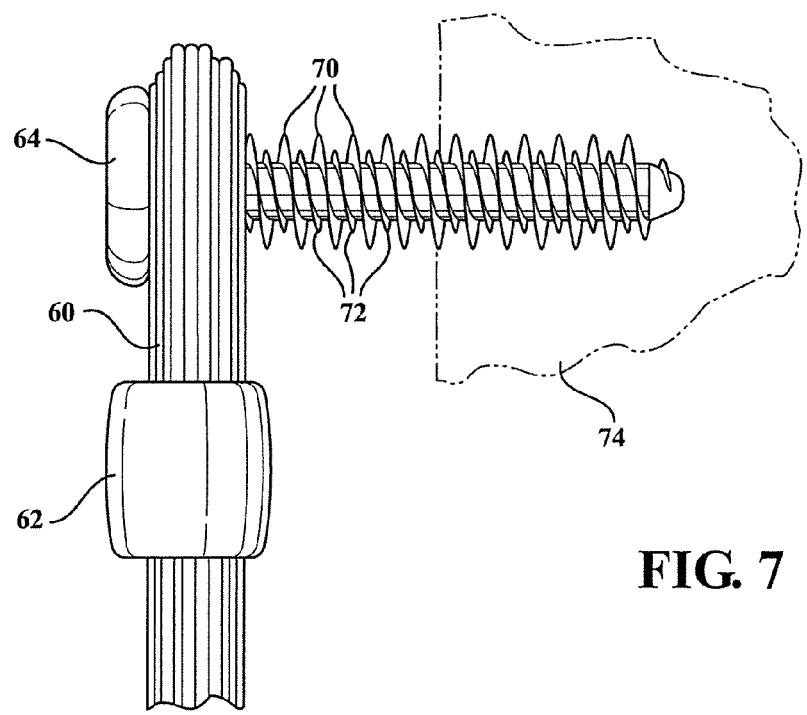
FIG. 7 is a side view illustration of the combination clamp and bone screw of FIG. 8.

Referring now to FIGS. 6 and 7, both perspective and side plan views are shown of an end looped plurality of ligaments, at 60, mounted to a bone (not shown) by a combination clamp 62 and bone screw 64 according to a further embodiment. As described previously, the ligaments 60 can be either natural or man-made and, upon being fashioned in the end-looped fashion illustrated, are fixed by application of the clamp 62.

As further shown, the clamp 62 can exhibit a tapered or non-linear three dimensional shape to accommodate the folded over ligament end-loop and can be constructed of a plastic or other suitable material and includes a split location 66 such as permitting the clamp to be forcibly manipulated in position around the looped end of the ligaments, following which they are snap-fit or tightened such that inner facing knurled patterns (see at 68 as is also shown in FIG. 10) engage and inwardly compress the overlapping ligament bunches. The screw 64 is pre-positioned during the initial folding of the ligament ends and is fixedly maintained about the inner looped end following installation of the clamp 62. As further shown in FIG. 7, the shaft portion of the screw 64 can exhibit varying thread profiles, see as shown at 70 and 72, this promoting gripping forces when installed within the user's bone (see as further shown in phantom at 74)

Figure 8:
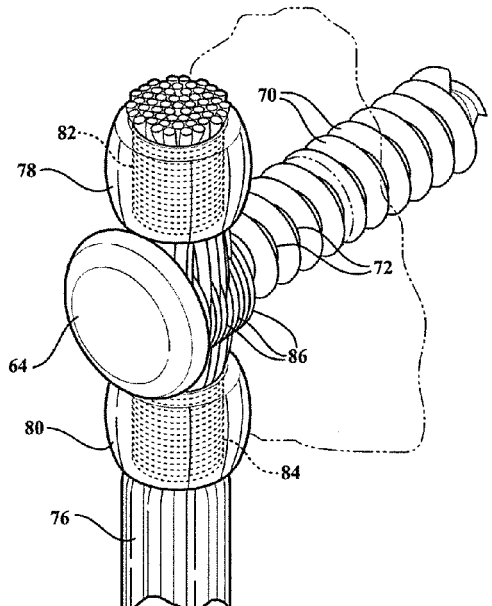
FIG. 8 is a perspective illustration of another mounting arrangement for securing an end plurality of ligaments to a bone and utilizing a pair of spaced apart ring clamps, between which a bone screw pierces through a fixed section of ligaments to anchor to a bone.

FIG. 8 illustrates a perspective view of a further mounting arrangement for securing an end plurality of ligaments, shown at 76, to a bone (not shown) and which utilizes a pair of spaced apart ring clamps 78 and 80, between which a modified version of the bone screw 64 pierces through a fixed section of ligaments and in order to anchor to a specified location of the bone. The ring clamps 78 and 80 each exhibit a split configuration allowing the clamps to separate into halves during assembly around the ligaments.

Inner circumferentially extending surfaces of the clamps each further exhibit inwardly facing and accordion-like serrated patterns, see in phantom at 82 and 84 respectively, which assist in providing the necessary compressive gripping engagement about the plural ligament strands. Although not clearly shown, it is understood that the ring clamps 78 and 80 can each further consist of assembled split portions, such as further utilizing any type of snap-fit or adjustable features to ensure secure and fixed location with respect to the ligaments.

The modified anchor screw 64 can again be constructed of a plastic or composite material and is typically pre-positioned in piercing fashion through the ligament strands before installation of the split rings 78 and 80. In combination with the varying thread patterns 70 and 72 previously described (see FIG. 7), a further plurality of increased diameter and narrower thickness threads are shown at 86 associated with the screw 64 and function to provide enhanced gripping of the ligaments 76, this preventing the screw 64 from inadvertently detaching from the ligaments during subsequent use and progressive fusing of the ligaments to the bone surfaces, and which is ensured by the clamping forces asserted by the adjoining ring clamps 78 and 80.

Figure 9:
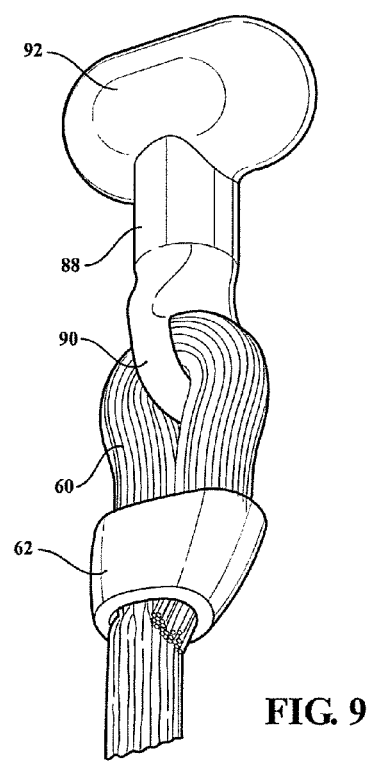
FIG. 9 is a perspective illustration of an end looped plurality of ligaments mounted to a bone by a combination intermediate clamp and end positioned anchor according to a still further embodiment.

FIGS. 9 and 10 illustrate a pair of environmental and separate perspective views, respectively of an end looped plurality of ligaments (again at 60 in FIG. 9 and referring to the previously described embodiment of FIG. 6) and which is mounted to a bone by a combination intermediate clamp (see again at 62 and according to that previously described in FIG. 6) as well as an end positioned anchor 88. The anchor 88 can be constructed of a plasticized or composite plastic material which replaces the bone screw 64 associated with the previous embodiment and also includes a first aperture defined end, see lower ring 90, for receiving the looped ligament strands 60 prior to the same be fastened to the (split ring assemble or solid one piece) clamp 62. An upper end of the anchor 88 includes a generally dual-end bulbous shaped portion 92, this corresponding to a recessed undercut pattern (not shown in this variant) associated with a machining process applied to an associated bone (also not shown) and to which is permanently secured the projecting portion 92 of the anchor 88.

Referring now to FIGS. 11, 12 and 13, a series of illustrations are shown in perspective environmental, side assembled and perspective exploded respectively of a ligament end mounting clamp, generally at 94, according to a still further configuration. The clamp 94 includes a bone securing undercut end-anchor assembly in the form of a projecting portion 96 (which is similar to the projection portion 92 in FIG. 10), and which is integrally formed with an elongated stem for supporting about an end of a ligament bunch 98 and which is inwardly compressible by a slidably installed ring clamp 100.

The exploded view of FIG. 13 best illustrates the configuration of the anchor assembly 94 and, in addition to the undercut engaging end 96, further shows an integrally extending stem consisting of first and second sections 102 and 104 (both extending from a common trunk 105 located in communication with an underside of the projecting portion 96), the individually branching sections 102 and 104 further separated by a pair of linear extending slots 106 and 108. As further shown, an inner profile of each of the stem sections 102 and 104 further exhibit a serrated pattern (at 110 and 112 in FIG. 13) which enable the clamp assembly to be pre-positioned over the extending end of the ligament bunch 98 as shown in FIG. 11.

At this point, the ring clamp 100, which exhibits a generally annular shape, is installed in a progressive sliding fashion over end-most (and slightly projecting) and generally semi-cylindrical shaped portions 114 and 116 associated with the stem sections 102 and 104, following which the ring clamp 100 seats within intermediate recessed surfaces 118 and 120 separating the end-most portions 114 and 116 with upper located portions of the stem sections 102 and 104. The dimensions of the recessed profile (see again FIG. 13) defined in the intermediate location of the clamp stem are such that the slidably engaged ring clamp 100 is fixedly seated in place (FIGS. 11 and 12) while exerting a sufficient compressive holding and gripping forces against the ligament bunch 98.

Additional features not specifically shown include the collar being height adjustable along the inwardly compressible stem in order to modify a clamping compressive force exerted on the ligament bunch. Also shown at 122 is an upper end aperture associated with the undercut engaging top end 96 through which projects a very end point of the ligament bunch, see further at 124 in FIGS. 11 and 12, and in order to promote ligament fusion to the interior profile of the bone (not shown) within which the undercut portion 96 is anchored.

FIGS. 14-17 disclose a series of perspective illustrations of a ligament end mounting clamp, generally at 94, according to a still further configuration similar to that previously described in FIGS. 11-13, but in which the fixed upper end mounted undercut anchor (at 96 in FIG. 11) has been reconfigured by the addition of a pair of semi-spherical undercut seating portions 126 and 128 and associated trigger mechanism for outwardly displacing the seating portions 126 and 128 from a modified housing 130 similar to a "T" connector like fitting associated with the end anchor. The trigger mechanism is initially identified by slot 132 positioned along a lengthened upper trunk end 133 of the interconnecting stem portion (see again lower communicating split stem sections 102 and 104) through which the ligament bunch 98 extends.

An actuating mechanism is incorporated into an upper end of the clamp housing and is connected to a button 134 (see triangular shaped actuating mechanism 135 in phantom in FIG. 16) seated within the slot 132 and which is actuated via a stem or rod 133 interconnecting the wedge 135 with the button 134 to travel upwardly along the length of the slot 132 concurrent with selectively upwardly/outwardly actuating or downwardly/inwardly retracting individual undercut seating portions 126 and 128. The initial retracted position of undercut seating portions 126 and 128 within the upper end housing 130 in FIG. 15 corresponds to an initial bone installation position of the anchor within a previously undercut location (see at 136 in FIG. 14 and which is communicated to an exterior of the bone via a narrowed neck 138), such undercut formation being known through the implementation and manipulation of appropriate medical drilling and routing tools.

The length and width dimensions of the sleeve shaped housing 130 (with inwardly retracted seating portions 126 and 128) is understood to be sufficient to permit insertion through the narrowed neck profile 138 of the bone. The trigger mechanism is subsequently engaged (by moving the button 134 upwardly along the slot 132) in order to cause the internal actuating mechanism, such as again the wedge type component 135 and which can also include a cam or bevel arrangement of some type, to outwardly displace the seating portions 126 and 128 from inside the housing 130 to the position shown in FIG. 14 and in order to permanently seat and anchor the anchor assembly within the undercut configuration of the bone. It is also envisioned that the triangular/wedge shaped element 135 can also exhibit an inner aperture (see perimeter defining inner wall 137) which permits the ligament bunch 124 to be pre-located through the interior of the wedge in the manner shown and so that the triangular wedge can be actuated without interfering with the positioning of the ligaments.

Figure 16:
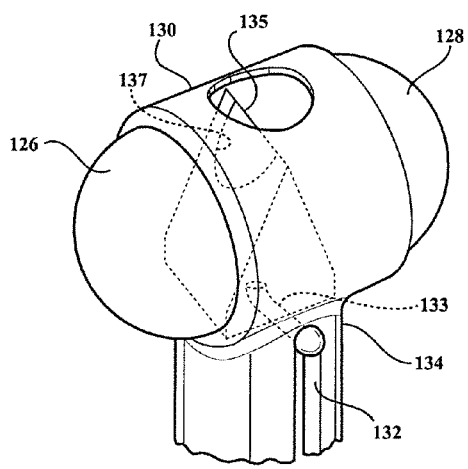
FIG. 16 is a succeeding illustration of the mounting clamp, similar to FIG. 14 and illustrating trigger mechanism displaced to an upper-most position corresponding to outward actuation of the seating portions from the sleeve shaped and cross wise end extending housing.

In a possible alternate arrangement to the wedge shaped component 135 depicted in FIG. 16, another possible example of a laterally displacing mechanism is representatively illustrated in FIG. 15 (which illustrates the anchor assembly without the ligament bunch 98) and in which are partially evident inner/opposing engaging locations 140 and 142 associated with the laterally displaceable seating portions 126 and 128. The seating portions 126 and 128 are biased outwardly by an alternately configured cam or other type displacing portion (this being further representatively shown in selected view of FIG. 17 as including a gear rack 141 which is mechanically linked at a lower end to the trigger button 134 and which, upon traveling upwardly, rotates a gear 143. The gear 143 in turn mounts and coactively rotates a pair of oppositely extending and exteriorly threaded shafts 145 which are seated within internally threaded pockets defined in the base of each seating projection 126 and 128 and, upon actuating, causes the portions 126 and 128 to oppositely and outwardly separate.

Figure 17:
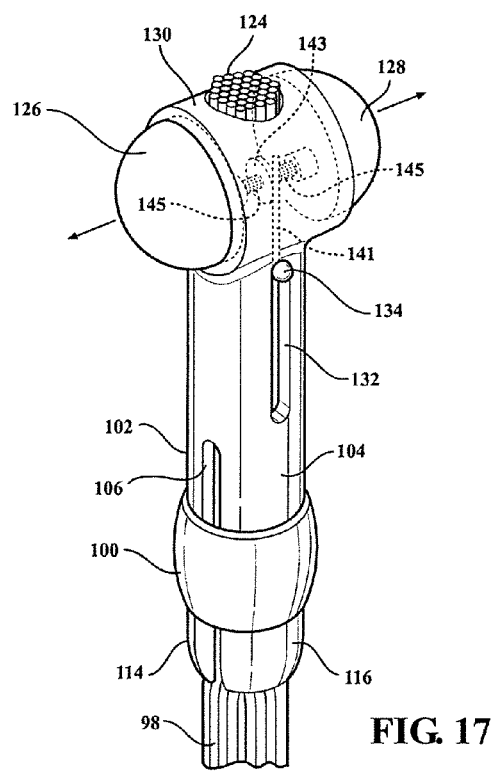
FIG. 17 is a somewhat enlarged and corresponding view to that shown in FIG. 14.

As previously described with reference to the embodiment of FIGS. 11-13, the gear actuating mechanism 143 and 145 can also be reconfigured differently than shown in FIG. 17 (such as by repositioning the rotating gear 143 and oppositely extending threaded drive shafts 145) in such a fashion that the ligament bunch 124 can remain permanently affixed to the anchor assembly. Further, and via the split stem arrangement with inwardly teethed and serrated surfaces combined with the provision of the ring clamp 100 which forcibly engages over the lower end portions 114 and 116 associated with the split stem 102 and 104, subsequently seats within the reduced intermediate recessed surfaces 118 and 120, separating the end-most portions 114 and 116 with upper located portions of the stem sections 102 and 104, this again in order to maintain a permanent gripping arrangement with the ligament bunch 98. As also previously described, the upper projecting ends 124 of the ligament bunch 98, being in contact with the inner undercut surface of the bone, also promote additional adhering growth to the associated bone.

FIGS. 18 and 19 disclose a pair of exploded and environmental assembled perspective views of another version ligament clamp assembly and in which a pair of ring-shaped and spaced apart clamps 146 and 148 are configured for gripping and compressing individual linear locations associated with first 151 and second 153 sections of ligaments located proximate to a damaged area. FIG. 18 is an enlarged view better showing the configuration of the pair of ligament compressing clamps 146 and 148, each of which are fairly identically constructed to the ring shaped clamp previously identified at 28 integrally incorporated into the overall clamping assembly referenced in the embodiment 10 of FIG. 1. In particular, each of the clamps 146 and 148 likewise include a first mounting end exhibiting a tab 150 and 152 (such as again further configuring a ramped or angled portion terminating in an end abutting shoulder) which is engageable within a slot 154 and 156 defined within an opposing receiving portion associated with the second mounting end.

Also illustrated is the incorporation of an angled incision, at 158, defined in the opposing and mating ends of the end to end abutting ligament sections 151 and 153 according to the further preferred configuration. As with the "V" notch configuration previously described, at 16-22 in FIG. 2, the 45° angled cut 158 referenced in FIG. 19 provides another non-limiting example of an increased surface splicing operation for creating a maximum area of inter-ligament growth or adhesion, such as during a healing process following initial reconditioning of the ligaments and application of the clamps (such as in situ within the patient).

The pair of ring shaped clamps in FIG. 18 again illustrate inwardly defined serrated teethed patterns, at 160 and 162, for enhancing its gripping properties when installed in compressing fashion over the ligament bunches 151 and 153. Upon installation, the projecting tabs 150 and 152 each include a progressing ramp (see at 163 for selected tab 152) terminating in an inner seating shoulder 164. The tab 150 is caused to deflect inwardly, see arrow 165, during passage therethrough of the ramp 163, and which is dimensioned to pass through the slot 154. Following this, an interconnected and narrowed neck 166 communicates within the slot 154 and whereby the resilient properties of the tab 150 bias it outwardly in the direction of arrow 168 to lock the clamp in place.

Figure 20:
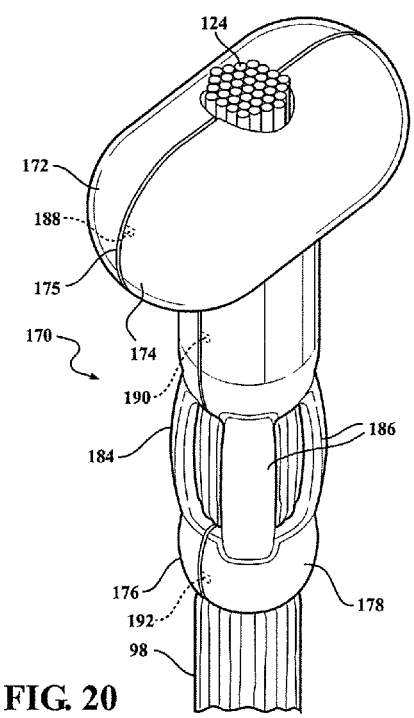
FIG. 20 is a perspective view of a ligament end mounting clamp according to a yet further variant and including a modified stem configuration for enhancing gripping of a plurality of ligaments of varying thicknesses.
Figure 21:
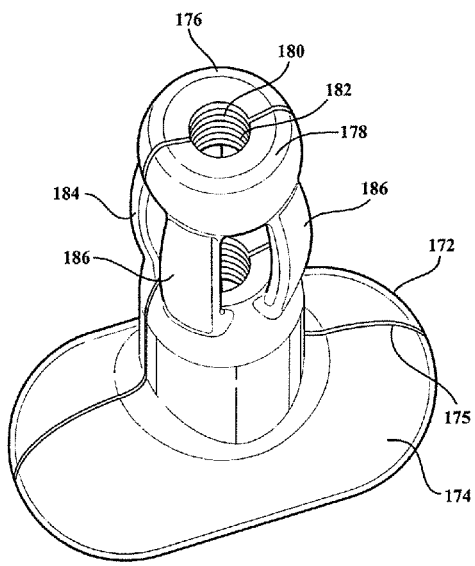
FIG. 21 is rotated perspective view of the clamp of FIG. 20 and further showing the first and second spaced apart and integrally formed semi-circular ring clamp portions with inner knurled surfaces, combined with the intermediately positioned, length extending and circumferentially spaced arms associated with a structural supporting portion of the stem.
Figure 22:
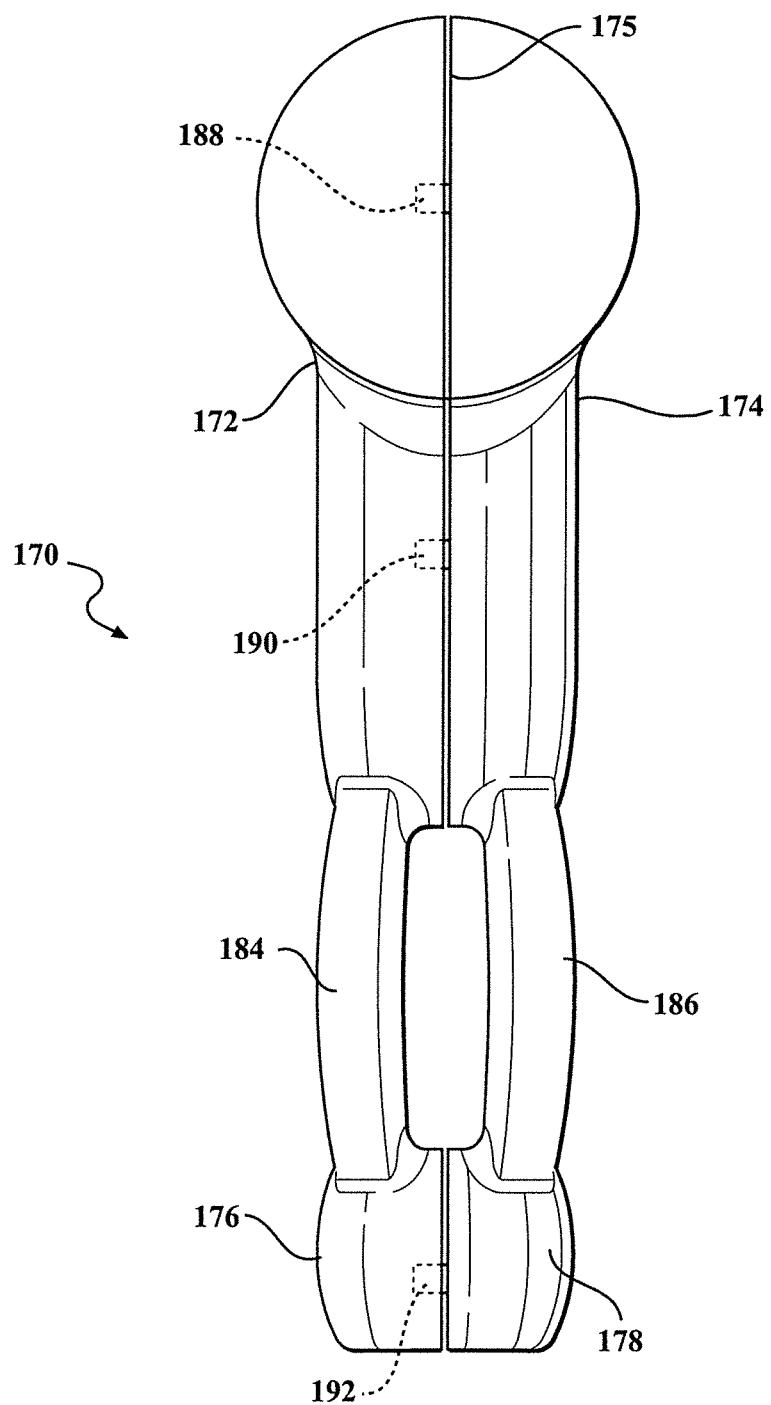
FIG. 22 is a side plan view illustrating the two piece snap-fit nature of the clamp design of FIG. 20 and further showing spaced apart engaging tabs for adjusting a spatial positioning of the first and second pieces relative to differently sized ligaments.

Referring finally to FIGS. 20-22 a related version of a ligament end anchor undercut clamp assembly, as generally shown at 170, is configured similar to that illustrated at 94 in FIG. 11, with the exception that the entire anchor (head) and stem portions are constructed as first 172 and second 174 split portions which are bounded by a central and length extending parting line 175. Also shown is a modified stem configuration which provides enhancing gripping of the plurality of ligaments 98, such as being of varying thicknesses.

FIG. 21 is a rotated (underside facing) perspective view of the clamp of FIG. 20 and further shows the provision of first 176 and second 178 spaced apart and integrally formed semicircular ring clamp portions, these further exhibiting inner knurled surfaces 180 and 182. Combined with intermediately positioned, length extending and circumferentially spaced arms 184 and 186 interconnecting an upper end of the stem with the bottom located ring clamp portions 176 and 178, the structural supporting stem provides both enhanced gripping of the end location of the ligament bunch 98 (such as further enhanced by the provision of the inwardly facing and knurled/serrated surfaces).

FIG. 22 is a side plan view illustrating the two piece snap-fit nature of the clamp design of FIG. 20 and further showing the feature of spaced apart engaging tabs, at 188, 190 and 192, located at respective head, stem and bottom ring clamp locations of selected split portion 174. In this fashion, the tabs 188, 190 and 192 biasingly engage mating locations associated with the other split portion 172 for adjusting a spatial positioning of the first and second split portion pieces relative to one another, such as in order to accommodate differently sized ligament bunches.

Having described my invention, other and additional preferred embodiments will become apparent to those skilled in the art to which it pertains, and without deviating from the scope of the appended claims.

I claim:

1. A clamp assembly for joining first and second ligament sections, comprising:
   a body including first and second lengthwise extending supports interconnected by a ring shaped clamping portion so that said supports are spatially arrayed relative to one another, said lengthwise extending supports further having gripping locations configured upon inwardly facing and opposing surfaces thereof;
   said ring shaped portion having a split location for dividing said ring portion into separable halves to which said supports are mounted;
   said body being flexible and openable at said split location so that an interior of said body is adapted to receive opposite extending ends of the ligament sections;
   a tab extending from a first of said separable halves past said split location; and
   a slot defined in a second of said separable halves and through which is engaged said tab in order to clamp said body about the ligament sections.

2. The clamp assembly as described in claim 1, further comprising an inner circumferential surface of said ring shaped clamp exhibiting knurled portions adapted to gripping the ligament sections.

3. The clamp assembly as described in claim 1, said inwardly facing and opposing surfaces of said lengthwise extending supports each further comprising a circumferential cross sectional profile.

4. The clamp assembly as described in claim 1, said tab further comprising an angled ramp edge extending from a first edge defined by said split and seating within said aperture defined by a second edge.

\* \* \* \* \*